United States Patent [19]

Suzuki et al.

[11] 4,425,127
[45] Jan. 10, 1984

[54] DISPOSABLE DIAPERS

[75] Inventors: Migaku Suzuki, Kawanoe; Kozo Ochi, Ehime; Takamitsu Igaue, Kawanoe, all of Japan

[73] Assignee: Uni-Charm Corporation, Ehime, Japan

[21] Appl. No.: 311,410

[22] Filed: Oct. 14, 1981

[30] Foreign Application Priority Data

Oct. 22, 1980 [JP]   Japan ................................ 55-148009

[51] Int. Cl.³ .............................................. A41B 13/02
[52] U.S. Cl. ..................................... 604/366; 604/369; 604/385
[58] Field of Search ........... 128/284, 286, 287, 290 R, 128/290 W; 604/389, 374, 366, 370, 372, 385

[56] References Cited

U.S. PATENT DOCUMENTS

| | | | |
|---|---|---|---|
| 2,862,251 | 12/1958 | Kalwaites | 128/290 W |
| 3,461,871 | 8/1969 | Foote | 128/284 |
| 3,794,033 | 2/1974 | Ryan | 128/284 |
| 3,920,017 | 11/1975 | Karami | 128/287 |
| 4,135,021 | 1/1979 | Patchell et al. | 128/290 W |
| 4,324,245 | 4/1982 | Mesek et al. | 128/287 |

*Primary Examiner*—C. Fred Rosenbaum
*Assistant Examiner*—Gene B. Kartchner
*Attorney, Agent, or Firm*—Fred Philpitt

[57] ABSTRACT

A disposable diaper is disclosed. This diaper includes an absorbent body forming a layer thicker in a crotch area than in the rest area, said thicker layer of the absorbent body defined in the crotch area pressed along both sides thereof, and elastic members located on both sides of the crotch area each made of a relatively wide material.

5 Claims, 13 Drawing Figures

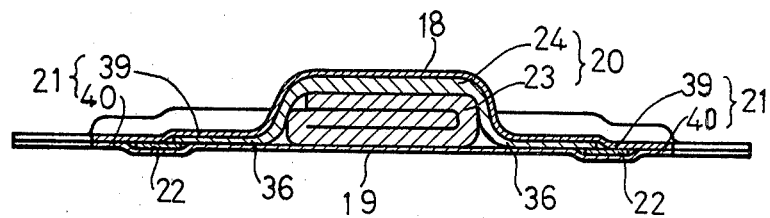
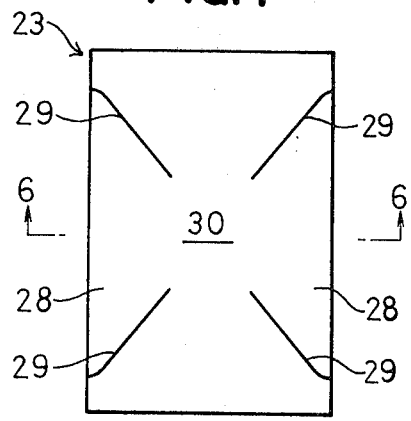
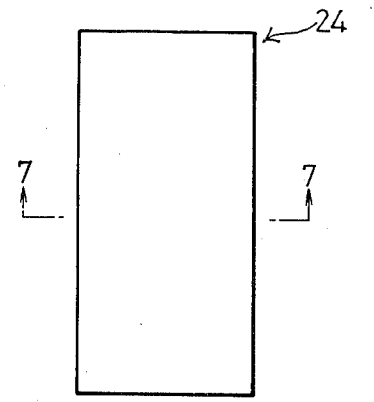
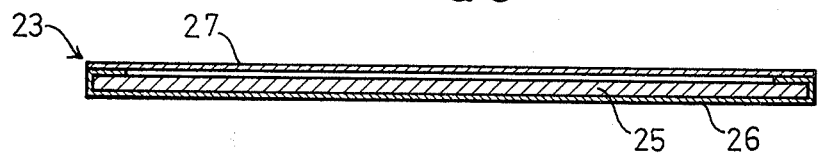
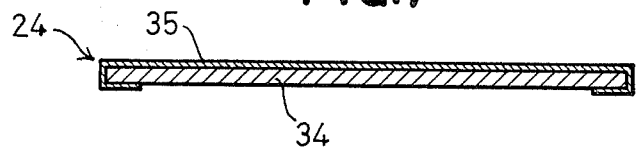

DISPOSABLE DIAPERS

TECHNICAL FIELD OF THE INVENTION

The present invention relates to an improvement for a disposable diaper designed to be worn by the infants, the aged, the sick persons or the like who can not dispose of excrement by their own efforts.

DISCLOSURE OF THE PRIOR ART

There have already been proposed and put to practical use disposable diapers of various types requiring no separate covers. These well-known diapers generally comprise a water-permeable top sheet adapted to be in contact with wearer's skin when worn on the wearer's body, a water-impervious back sheet adapted to be kept out of contact with the wearer's skin, a semi-rigid absorbent body interposed between said two sheets, opposite side flaps having a flexibility higher than said absorbent body, and elastic members arranged for elastical contraction and expansion occurring longitudinally in the associated ones of said side flaps, wherein said absorbent body comprises, as its principal material, fluffed pulp in many cases, a sheet of tissue paper is applied to top and bottom surfaces of said absorbent body, respectively, and the respective inner surfaces of said top and back sheets are bonded to the associated ones of said tissue paper sheets so that said absorbent body is provisionally fixed between these two sheets of tissue paper. These well-known diapers include the diaper shaped in so-called "hour-glass" having the crotch area formed narrower than the rest area and the diaper shaped in a simple rectangle, the former being superior to the latter in its tightness around leg. Typical embodiments of the former are disclosed by U.S. Pat. No. 3,860,003 and have been put to practical use.

However, the conventional diapers inclusive of the particular one disclosed by said U.S. Patent have been disadvantageous in that the absorbent body substantially consisting of fluffed pulp is relatively apt, furing use of handling, to be deformed into a button-shaped clump which, in turn, gives the wearer a uncomfortable feeling of foreign matter and causes leakage of liquid excrement, since said absorbent body is merely fixed in a provisional manner between the top and back sheets by the sheets of tissue paper, as previously mentioned. Particularly with the diaper disclosed by said U.S. Patent which has said absorbent body shaped in "hour-glass", the narrower width thereof in the crotch area correspondingly reduces the absorbing capacity for liquid excrement and causes leakage of liquid excrement.

In order that the side flaps of the diaper adapted to be applied around legs exert no tightly localized pressure around legs along lines and effectively prevent leakage of liquid excrement, it is preferred that the elastic member secured in each of said side flaps is relatively wide so as to have a relatively large area over which the elastic member is pressed against the wearer's skin. The well-known diapers using such elastic members is disclosed by Publication No. 54-133938 of Japanese Patent Application (unexamined) corresponding to U.S. Patent Application Ser. No. 892,628, wherein said elastic members, however, are not only poor in their cushion-like action in direction of the thickness but also not suitable for conformable but soft application of the side flaps around legs, and have no other function than pressing said side flaps around legs. Although it is claimed to be formed relatively wide, each of these elastic members meet only the minimum requirement for prevention of a painfully localized pressure from being applied around leg along a line and this prior art neither intends nor teaches the effect of enlarging the elastic member's contact area around leg while effectively preventing leakage of liquid excrement by absorption thereof.

OBJECT OF THE INVENTION

It is a principal object of the present invention to provide a disposable diaper having a semi-rigid absorbent body substantially consisting of fluffed pulp coverd at least at top and bottom surfaces with hydrophobic netty sheets, respectively, and fixedly bonded by said netty sheets at least to an inner surface of a back sheet so that said absorbent body's deformation is effectively avoided and liquid excrement once absorbed by said absorbent body is prevented from flowing backward and then soaking through the top surface of the diaper.

It is another principal object of this invention to provide a disposable diaper having an absorbent body shaped in so-called "hour-glass", wherein at least the portion of said absorbent body in a crotch area is formed thicker than the rest area and thereby the absorbing capacity in said crotch area may be improved.

It is still another principal object of this invention to provide a disposable diaper having a first side flap containing therein a compressed, thin semi-rigid absorbent layer consisting of fluffed pulp covered with hydrophobic netty sheets so that absorption and diffusion of liquid excrement may occur also in said side flap and said absorbent layer's deformation may be effectively prevented.

It is further another principal object of this invention to provide a disposable diaper having a relatively wide water-absorptive and air-permeable elastic member serving also as an effective cushion, said elastic member being incorporated into a first side flap and a second side flap or the second side flap only so as to improve absorbing capacity of these side flaps, to achieve conformable but soft application of said side flaps around leg, thereby to prevent leakage of liquid excrement around legs, and to improve air-permeability between the interior and the exterior of the diaper for effective prevention of stuffiness generated in the diaper.

These and other objects of the present invention will be apparent from the following description of the invention.

SUMMARY OF THE INVENTION

In accordance with the present invention, there is provided an improvement for a disposable diaper having a water-permeable top sheet, a water-impervious back sheet, a semi-rigid absorbent body interposed between these two sheets and formed narrower in a crotch area, side flaps outwardly extending from laterally opposite side edges of said absorbent body and formed by said top and back sheets at least in the crotch area, and elastic members secured in said side flaps for longitudinally elastic contraction and expansion, the improvement lying in that at least the portion of the semi-rigid absorbent body extending in said crotch area is formed thicker than the rest area; pressed semi-rigid absorbent members extend outwards from laterally opposite side edges of said thicker portion; said elastic members comprise relatively wide material having a superior cushion property.

BRIEF DESCRIPTION OF THE DRAWINGS

The invention will be better understood from the following description taken in reference with the accompanying drawings in which:

FIG. 3 is an enlarged cross-sectional view taken along line 3—3 of FIG. 1;

FIG. 4 is a plan view of a first absorbent member in an unfolded configuration;

FIG. 5 is a plan view of a second absorbent member in an unfolded configuration;

FIG. 6 is an enlarged cross-sectional view taken along line 6—6 of FIG. 4;

FIG. 7 is an enlarged cross-sectional view taken along line 7—7 of FIG. 5;

DETAILED DESCRIPTION OF THE INVENTION

Figure 1:
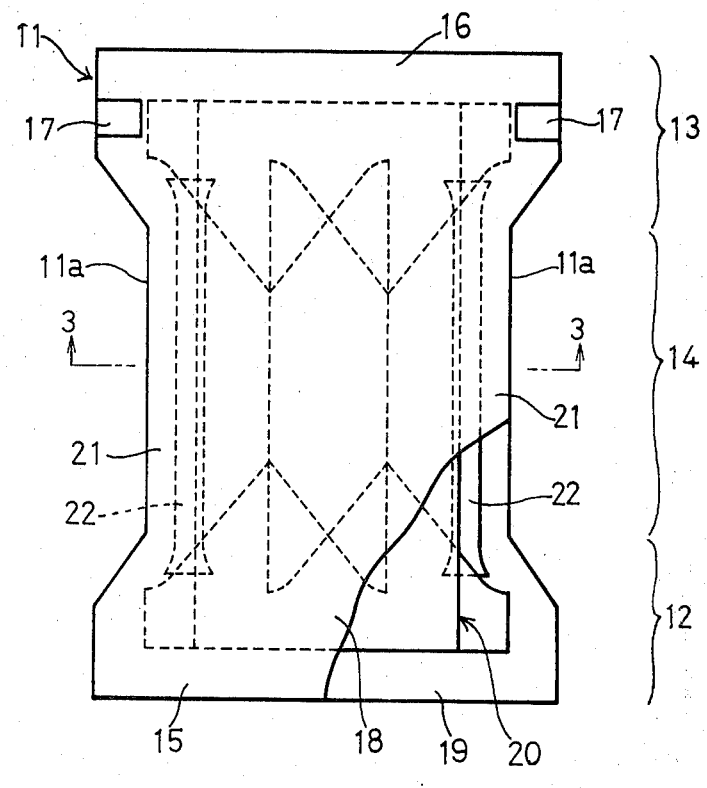
FIG. 1 is a plan view of a diaper of this invention in an unfolded configuration as seen from the top side.
Figure 2:
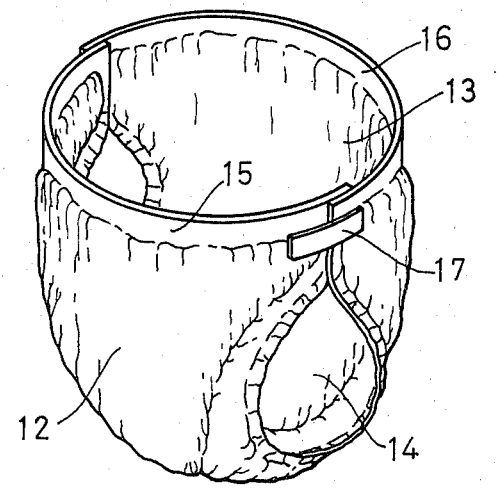
FIG. 2 is a perspective view of the diaper in its configuration as applied to a wearer's body.

In FIGS. 1 and 2, a preferred embodiment of a disposable diaper according to the present invention is shown in a typical arrangement. The diaper generally designated by 11 has a front portion 12, a back portion 13, a crotch area 14, and front and back waist portions 15, 16, wherein the diaper 11 adapted to be applied to a wearer's body by adhesively securing strips of fastening tape 17 respectively attached to opposite side ends of the back waist portion 16 to the corresponding side ends of the front waist portion 15. The diaper 11 further includes a water-permeable top sheet 18 adapted to be in contact with the wearer's skin when worn on the wearer's body, a water-impervious back sheet 19 adapted to be kept out of contact with the wearer's skin, a semi-rigid absorbent body 20 interposed between said two sheets, opposite side flaps 21, and elastic members 22 for longitudinally elastic contraction and expansion of the associated side flaps.

Figure 8:
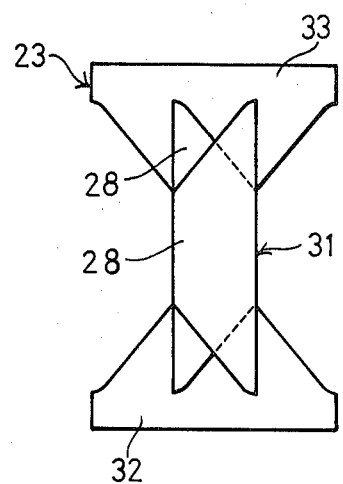
FIG. 8 is a plan view of the first absorbent member with laterally opposite side edges folded.
Figure 9:
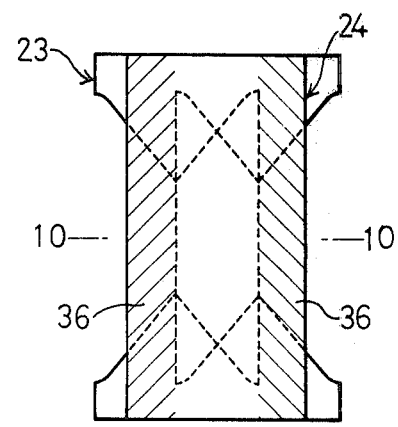
FIG. 9 is a plan view of the first absorbent member of FIG. 8 with the second absorbent member laid upon the top surface of said first absorbent member.
Figure 10:
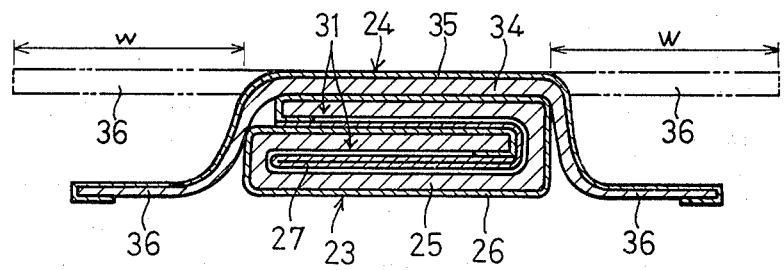
FIG. 10 is a cross-sectional view taken along line 10—10 of FIG. 9.

In FIGS. 3 through 10 and FIG. 12, details of the semi-rigid absorbent body 20 are shown. The absorbent body 20 comprises, as shown, a first absorbent member 23 and a second absorbent member 24. As will be apparent from FIGS. 4 and 6, the first absorbent member 23 comprises a fluffed pulp layer 25 covered at its bottom surface and opposite side edges with a hydrophobic netty sheet 26 while at its top surface with tissue paper 27, and provided with oblique slits 29 so as to form, on both sides thereof, trapezoidal portions 28 which are to be folded onto a central portion 30 so that the one of the two trapezoidal portions is laid upon the other, as seen in FIG. 8. The first absorbent member 23 thus presents a shape of hour-glass characterized by a narrower folded portion 31 extending in said crotch area 14 of the diaper and relatively wide portions 32, 33 extending in said front portion 12 and back portion 13 of the diaper, respectively. Although the folded portion 31 is shown as formed with the respective trapezoidal portions 28 laid upon one another, the respective portions 28 may be mutually opposed along their inner edges instead of being laid upon one another, depending on the thickness of the fluffed pulp layer 25 and the width of the portion 31 to be formed. The width and the length of the portion 31 depend, in turn, on the size of the diaper to be formed. The second absorbent member 24 has a width larger than the portion 31 of the first absorbent member 23 but narrower than the portions 32, 33 of the first absorbent member 23 and the same length as the first absorbent member 23. The second absorbent member 24 comprises a fluffed pulp layer 34 which is covered at its top surface and opposite side edges with a hydrophobic sheet 35, as shown by FIGS. 5 and 7, and laid upon the top surface of the first absorbent member 23 as shown by FIGS. 3, 9 and 10. Portions of said member 24 extending outwards from the opposite side ends of the folded portion 31 of said member 23, i.e., the portions 36 of said member 24 shown by oblique lines in FIG. 9 and designated by W in FIG. 10 are pressed in direction of the thickness so as to be bestowed with a semi-rigidity.

Thus, the portion of the absorbent body extending in said crotch area 14 defines the thickest portion and conformably applied to the wearer's crotch and increases the liquid excrement absorbing capacity at this portion. The respective semi-rigid portions 36 formed on the opposite sides of said portion are the thinnest portions and each containing therein the fluffed pulp layer 34 compressed to a high density, thus improving the absorptive and diffusive effect for liquid excrement. These portions 36 also serves to prevent displacement of the first absorbent member 23 by supporting the outer edges of the folded portion 31. The fluffed pulp layer 34 in each of these portions 36 is compressed, so these portions 36 are substantially equal to or slightly higher in flexibility than the absorbent body 20 but the conformable contact around the wearer's legs is never impaired thereby, since these portions 36 are provided with relatively wide water-absorptive elastic member 22, respectively.

Figure 11:
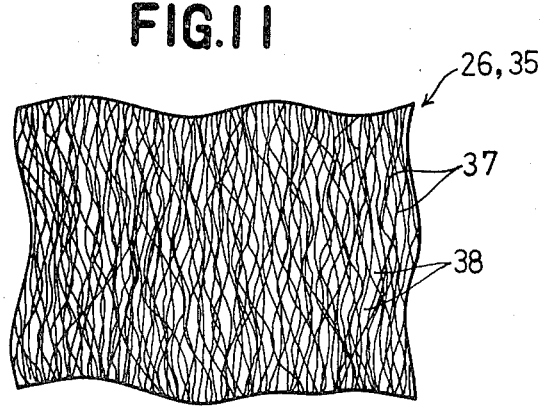
FIG. 11 is a fragmentary enlarged plan view of a hydrophobic netty sheet.

The hydrophobic netty sheets 26, 35 are obtained by a process comprising steps of adding a suitable foaming agent to independent or mixed hydrophobic resin(s) such as polypropylene, polyethylene and vinyl chloride, melting this mixture within an extruder, extruding and simultaneously foaming the melt for molding, and are available under the trade name "SHARNET" from Inmont Corporation, New York, N.Y., U.S.A. Such sheets 26, 35 comprise, as shown by FIG. 11, strands of tissue 37 each looking just like a continuous filament. These strands, partially connected with one another to form countless meshes 38, are thin and light, and have an elasticity in the direction transversely of the respective strands 37, i.e., in direction of the width. These sheets 26, 35 function, covering the first and second absorbent members 23, 24, respectively, to hold the surfaces of these members when these members are subjected be bending and tensile stresses during use or handling of the diaper so that the fluffed pulp layers 25, 34 contained in these members, respectively, may be effectively prevented from being deformed and liquid excrement once absorbed by the absorbent body 20 may be also prevented from flowing back towards the top surface and then soaking through the top sheet 18. Although these sheets 26, 35 are shown as used in the manner that a single sheet is associated with each of the first absorbent member 23 and the second absorbent member 24, a plurality of sheets may be used for the respective members 23, 24. It is certainly preferred that said sheets 26, 35 are present also within the absorbent body 20 as shown, but it should be understood that these sheets may be arranged to cover only the surface of the absorbent body 20.

The absorbent body 20 thus comprising the first absorbent member 23 and the second absorbent member 24, and the portions 36 of the second absorbent member 24 extending outwards from the opposite side edges of said absorbent body 20 are retained interposed between the top sheet 18 and the back sheet 19. Each of the side flaps 21 comprises a first side flap 39 being formed by interposing the portion 36 between the top sheet 18 and the back sheet 19 at the portion of the absorbent body 20 extending outwards from the associated side edge of the folded portion 31 while said second side flap 40 being formed by bonding together the top sheet 18 and the back sheet 19 at the portion extending outwards from the side edge of the associated portion 36, so that the side flaps 21 may have a high flexibility and form effective seals around the wearer's legs in cooperation with the elastic members 22 as will be described in details.

Figure 12:
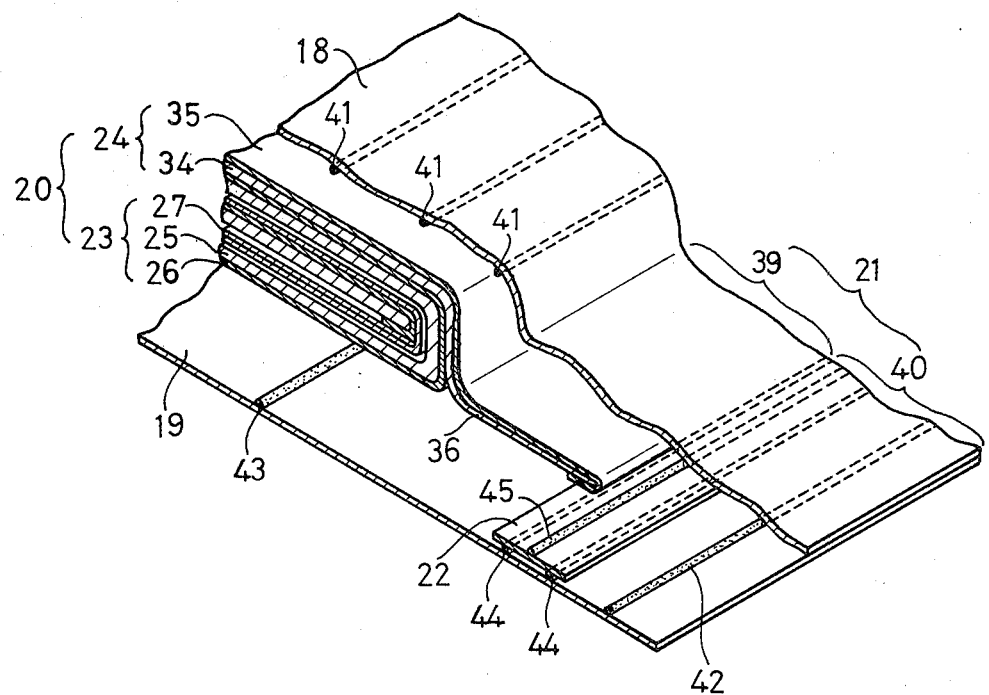
FIG. 12 is a perspective view, partially broken away, of a portion in which an elastic member is incorporated.

The top sheet 18 and the back sheet 19 are identical to each other and have cut-away portions 11a at their opposite sides. As material of the top sheet 18, the water-permeable sheet which has generally been used for the disposable diaper may be used here also, but, preferably, nonwoven fabric using no fiber binder and, more preferably, nonwoven fabric obtainable by the well-known treatment of water jet streams is used. More specifically, such nonwoven fabric is obtained by subjecting fibrous web to the water jet streams so that individual fibers are inter-entangled without use of any fiber binder. Methods of producing such nonwoven fabric are disclosed, for example, in Publication No. 48-13749 of Japanese Patent Application corresponding to U.S. Pat. No. 3,493,462. The nonwoven fabric thus obtained is sufficiently soft and bulky to be safely and comfortably applied to soft and delicate skin of the infant. As material of the back sheet 19, flexible plastic film of, for example, polyethylene which has generally been used for the disposable diaper may be used. As shown by FIG. 12, the inner surface of the top sheet 18 is provided at the central zone with hot melt adhesive 41 applied along lines at suitable intervals while the inner surface of the back sheet 19 is provided at opposite outer edges with hot melt adhesive 42 applied along lines and at the central zone with hot melt adhesive 43 also along lines. In a completed state of the diaper 11 as shown by FIGS. 1, 3 and 12, therefore, the respective inner surfaces of the top sheet 18 and the back sheet 19 are fixedly bonded by said adhesives 41, 43 to the hydrophobic netty sheets 26, 35 respectively lying on the top and bottom surfaces of the absorbent body 20 and the portions 36. Furthermore, the inner surfaces of the top sheet 18 and the back sheet 19 are bonded to each other by said adhesive 42 along their outer edges. As a result, the absorbent body 20 and the portions 36 are completely and fixedly covered with the top sheet 18 and the back sheet 19.

Figure 13:
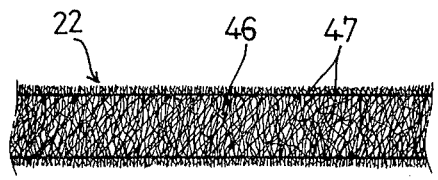
FIG. 13 is a fragmentary enlarged cross-sectional view illustrating another embodiment of the elastic member.

As seen in FIGS. 1 and 12, each of the elastic members 22 is shaped in a tape having an effective width of 10 to 50 mm, preferably, 20 to 40 mm, extending within the second side flap 40 in overlapping relationship with the bottom surface of the semi-rigid absorbent portion 36, and bonded, in its longitudinally tensioned state, by the adhesive 44 applied on its bottom surface in two parallel lines extending along its both side edges to the inner surface of the back sheet 19 and by the adhesive 45 applied on its top surface along a central line to the inner surface of the top sheet 18. When the elastic member 22 has been thus secured, a distance from the outer edge of the semi-rigid absorbent portion 36 to the effective outer edge of said elastic member 22, more precisely, to the outermost adhesive 44 of all the adhesives applied on said member 22 should be 19.1 mm or shorter. The term "effective width" of the elastic member 22 hereby means a distance between the innermost adhesive 44 and the outermost adhesive 44 applied on said member 22, and the portion of this effective width functions as elastical contraction and expansion of the side flap. Though the elastic member 22 is shown at its inner edge and the outer edge of the portion 36 lie one upon another, it should be understood that said inner edge and said outer edge may be in contact with each other or closely adjacent to each other, instead of thus lying one upon another. As material of the elastic member 22, the water-absorptive and air-permeable material which has generally been used for bandage, and preferably soft polyesters-urethane foam is used. Such polyesters-urethane foam has a superior cushion property also in direction of the thickness and thereby can be comfortably pressed around the wearer's leg. More preferably, a sheet of foamed body having fibers planted thereon is used. Such sheet comprises, as shown by FIG. 13, a sheet 46 of soft foamed urethane having a plurality of water-absorptive fibers 47 which are inter-entangled and planted on said sheet 46 by the treatment of water jet streams, and is superior in its water absorbing and retaining characteristic to the simple foamed urethane. When the elastic member 22 made of such material is arranged along the borderline of the first side flap 39 and the second side flap 40 or within the second side flap 40 only, the liquid excrement absorbing capacity in these flaps is thereby improved and leakage of liquid excrement around the wearer's leg is effectively avoided. Thickness of the elastic member 22 may be in the order of 0.5 to 2.5 mm to achieve the above mentioned effect, but the thickness of said elastic member 22 is never limited to such specific values.

With the arrangement as has been described hereinbefore, it is apparent that the diaper 11 of this invention can fully achieve all the objects set forth above. Finally, the effect caused from the diaper 11 of this invention will be supplementarily considered. Although most of liquid excrement is absorbed and retained by the semi-rigid absorbent body 20 in the crotch area 14, which has its absorbing capacity improved according to the invention as mentioned above, an excessive quantity of liquid excrement may sometimes soak through said absorbent body 20 and reach the semi-rigid absorbent portions 36 at both sides of said absorbent body 20. However, these semi-rigid absorbent portions 36 respectively contain therein the fluffed pulp layers compressed to a sufficiently high density for effective absorption and diffusion of such excessive quantity of liquid excrement. Even when liquid excrement is further excessive, the elastic member 22 arranged on the opposite outer sides of said portions 36 may satisfactorily function to prevent leakage of liquid excrement around the wearer's legs since the elastic members 22 are in contact with legs along a sufficiently large area. Moreover, the elastic members 22 themselves are air-permeable and therefore a kind of ventilation is established between the interior and the exterior of the diaper when worn on the body, so that there occurs no stuffiness in the diaper which is uncomfortable for the wearer.

What is claimed is:

1. In a disposable diaper having a water-permeable top sheet, a water-impervious back sheet, a semi-rigid absorbent body primarily composed of fluffed pulp interposed between these two sheets and formed narrower in a crotch area, side flaps extending outwardly from laterally opposite side edges of said absorbent body, and elastic members secured in said side flaps for longitudinally elastic contraction and expansion, the improvement comprising:
   (A) said absorbent body comprising a first absorbent member and a second absorbent member, each composed of fluffed pulp,
      (1) said first absorbent member
         (a) having a generally rectangular configuration and a hydrophobic netty sheet at least covering its bottom surface,
         (b) having partially cut out side panels that are separated by an intermediate panel, said side panels being folded inwardly towards each other so that said side panels and said intermediate panel form a folded 3-layer thickness of absorbent material,
      (2) said second absorbent member
         (a) having a generally rectangular configuration with a width that is greater than the width of said folded 3-layer thickness of absorbent material,
         (b) that has at least its top surface covered with a hydrophobic netty sheet, and
         (c) that lies upon the top surface of said first absorbent member,
   (B) inner and outer side flaps located on each side of said diaper
      (1) said inner side flap being composed of the portion of the side of said second absorbent member that extends outwardly from said folded 3-layer thickness of the first absorbent material, said portion including an underlying layer of hydrophobic netty material, and said portion being interposed between said top and back sheets, and
      (2) said outer side flap being located outwardly from said inner side flap and being composed of said top and back sheets bonded to each other,
   (C) said elastic member located in said side flaps and being in the form of a foamed tape having a length of 10–50 mm and being positioned at a distance of not more than 19.1 mm outwardly from the side of said second absorbent member.

2. A disposable diaper as defined by claim 1 wherein the elastic member is composed of polyester-urethane foam.

3. A disposable diaper as defined by claim 1 wherein said elastic member is bonded to at least the inner surface of the back sheet by at least two spaced apart and longitudinally extending strips of adhesive agent, extending longitudinally and spaced from one another transversely of said elastic member.

4. A disposable diaper according to claim 1 wherein said side panels of (A) (1) (b) are shaped like trapezoids.

5. A disposable diaper according to claim 1 wherein said elastic member is air-permeable.

* * * * *